(12) United States Patent
Fujimori

(10) Patent No.: US 7,959,562 B2
(45) Date of Patent: Jun. 14, 2011

(54) BODY-INSERTABLE APPARATUS, IN-VIVO INFORMATION ACQUIRING SYSTEM, AND BODY-INSERTABLE APPARATUS MANUFACTURING METHOD

(75) Inventor: Noriyuki Fujimori, Nagano (JP)

(73) Assignee: Olympus Medical Systems Corp., Tokyo (JP)

( * ) Notice: Subject to any disclaimer, the term of this patent is extended or adjusted under 35 U.S.C. 154(b) by 1172 days.

(21) Appl. No.: 11/699,127

(22) Filed: Jan. 29, 2007

(65) Prior Publication Data
US 2007/0191683 A1 Aug. 16, 2007

Related U.S. Application Data

(63) Continuation of application No. 11/572,784, filed on Jan. 26, 2007.

(51) Int. Cl.
*A61B 1/06* (2006.01)
(52) U.S. Cl. ...................................................... 600/160
(58) Field of Classification Search .................. 600/101, 600/109, 117, 118, 160
See application file for complete search history.

(56) References Cited

U.S. PATENT DOCUMENTS

| 4,439,197 A * | 3/1984 | Honda et al. ............... 604/891.1 |
| D543,272 S * | 5/2007 | Gilad et al. ..................... D24/113 |
| 7,647,090 B1 * | 1/2010 | Frisch et al. .................... 600/473 |
| 2002/0109774 A1 | 8/2002 | Meron et al. |
| 2002/0156347 A1 * | 10/2002 | Kim et al. ..................... 600/160 |
| 2002/0198439 A1 | 12/2002 | Mizuno |
| 2003/0023150 A1 | 1/2003 | Yokoi et al. |
| 2004/0171914 A1 * | 9/2004 | Avni ............................. 600/160 |
| 2005/0004474 A1 | 1/2005 | Iddan |
| 2005/0043583 A1 | 2/2005 | Killmann et al. |
| 2005/0049462 A1 * | 3/2005 | Kanazawa ..................... 600/170 |
| 2005/0143624 A1 | 6/2005 | Iddan |
| 2006/0167339 A1 * | 7/2006 | Gilad et al. .................... 600/101 |
| 2006/0224040 A1 * | 10/2006 | Khait et al. .................... 600/102 |
| 2008/0021270 A1 * | 1/2008 | Suzushima et al. ........... 600/109 |
| 2008/0045792 A1 * | 2/2008 | Shimizu et al. ............... 600/118 |
| 2008/0269664 A1 * | 10/2008 | Trovato et al. ................... 604/20 |
| 2009/0281380 A1 * | 11/2009 | Miller et al. ................... 600/109 |

FOREIGN PATENT DOCUMENTS

| JP | 2003-019111 | 1/2003 |
| JP | 2003-70728 | 3/2003 |
| JP | 2004-129949 | 4/2004 |
| JP | 2004-344655 | 12/2004 |
| JP | 2005-503182 | 2/2005 |
| WO | WO 02/054932 A2 | 7/2002 |
| WO | WO 03/069913 A1 | 8/2003 |

* cited by examiner

OTHER PUBLICATIONS

U.S. Office Action dated Sep. 21, 2010.

*Primary Examiner* — Philip R Smith
(74) *Attorney, Agent, or Firm* — Scully, Scott, Murphy & Presser, P.C.

(57) ABSTRACT

An object of the present invention is to make it possible to closely examine a specific region by making most use of an advantage of a compound-eye capsule endoscope that picks up images of an interior of a body cavity forward and backward in a movement direction of a capsule casing. By disposing imaging devices of respective imaging blocks in a capsule casing while having a relationship between arrangement directions of the imaging devices, e.g., making upward and downward directions U and D coincident with each other, a correspondence/positional relationship between the images picked up by the imaging devices is clear when the specific region such as an affected part in the body cavity is to be observed using the respective images forward and backward in the movement direction, thereby facilitating close examination on the specific region using the both images.

9 Claims, 13 Drawing Sheets

BODY-INSERTABLE APPARATUS, IN-VIVO INFORMATION ACQUIRING SYSTEM, AND BODY-INSERTABLE APPARATUS MANUFACTURING METHOD

CROSS-REFERNCE TO RELATED APPLICATIONS

This application is a continuation application of U.S. application Ser. No. 11/572,784 filed on Jan. 26, 2007, the content of which is incorporated herein by reference.

TECHNICAL FIELD

The present invention relates to a body-insertable apparatus such as a compound-eye capsule endoscope, an in-vivo information acquiring system, and a method of manufacturing a body-insertable apparatus.

BACKGROUND ART

In recent years, development of a swallowable capsule endoscope is underway in the field of endoscopes. This capsule endoscope includes an imaging function and a radio function. The capsule endoscope functions to move in patient's organs, e.g., the esophagus, the stomach and the small intestine according to peristaltic movements of the organs and to sequentially pick up in-vivo images after it is swallowed from a patient's mouth for observation of the interior of a body cavity until being naturally discharged (see, for example, Patent Document 1).

During the movement of the capsule endoscope in the body cavities, image data picked up in the body cavities by the capsule endoscope is sequentially transmitted to the outside of the patient's body by radio communication and accumulated in a memory provided in a receiver outside of the patient's body. A doctor or a nurse can diagnose the patient based on images displayed on a display based on the image data accumulated in the memory.

Patent Document 1: Japanese Patent Application Laid-Open No. 2003-19111

Patent Document 2: Specification of U.S. Patent Application Publication No. 2002/109774

DISCLOSURE OF INVENTION

Problem to be Solved by the Invention

Meanwhile, as the capsule endoscope of this type, a single-eyed endoscope that picks up only images of the body cavities (hereinafter, "body cavity images") forward in the direction of the movement of the endoscope has been generally used. Recently, however, a compound-eye capsule endoscope that picks up images forward and backward in the direction of the movement of the endoscope has been proposed with a view of enlarging the field of view during the observation of, for example, the esophagus (see, for example, Patent Document 2). This compound-eye capsule endoscope is configured as follows. A plurality of imaging blocks each including an illuminating unit such as an LED for illuminating the interior of each body cavity and an imaging device such as a CCD for picking up body cavity images is provided back and forth in a capsule casing. The imaging blocks pick up images forward and backward in the direction of the movement of the capsule endoscope in the body cavity.

Generally, the capsule endoscope passes through the esophagus at high speed. Due to this, the single-eyed capsule endoscope often overlooks an abnormal site in the esophagus. If the compound-eye capsule endoscope is employed, it can picks up more images even within short time because of capability of picking up images forward and backward in the direction of the movement of the capsule endoscope. It is, therefore, possible to reduce the frequency of overlooking abnormal sites. The small intestine is constituted by a relatively straight lumen, so that it generally suffices to observe the small intestine from one side using the single-eyed capsule endoscope. The esophagus is largely constituted by a straight lumen. However, it has an asymmetric shape forward and backward in the direction of the movement such as the esophageal orifice of the stomach. Due to this, if the compound-eye capsule endoscope that can observe a region from both forward and backward in the direction of the movement of the endoscope is employed, the field of view can be secured.

The compound-eye capsule endoscope disclosed in the Patent Document 2 or the like was proposed in such background. However, it is only described therein that the imaging devices pick up the images both forward and backward in the direction of the movement. Specific configurations and the like such as how to make effective use of advantages of the compound-eye capsule endoscope are not at all mentioned.

The present invention has been achieved in view of the above-stated respects. It is an object of the present invention to provide a body-insertable apparatus, an in-vivo information acquiring system, and a method of manufacturing a body-insertable apparatus capable of closely investigating a specific region while making most use of the advantages of a compound-eye capsule endoscope in that the field of view can be enlarged by picking up images forward and backward in the direction of the movement of a capsule casing in the body cavity.

Means for Solving Problem

A body-insertable apparatus includes a capsule casing; a plurality of illuminating units, provided in the capsule casing, that illuminates an interior of a body cavity; and a plurality of imaging devices, provided in the capsule casing while arrangement directions of the plurality of imaging devices are associated with one another, that constitute imaging blocks, respectively together with the paired illuminating units, and that pick up images of the interior of the body cavity at backward and forward in a movement direction of the capsule casing.

In the body-insertable apparatus according to the invention, each of the imaging devices of the respective imaging blocks may be disposed in the capsule casing while making upward and downward directions of the imaging devices coincide with one another.

In the body-insertable apparatus according to the invention, each of the imaging devices of the respective imaging blocks may be disposed in the capsule casing while making upward and downward directions of the imaging devices relatively deviated from one another by a predetermined angle.

In the body-insertable apparatus according to the invention, each of the imaging devices of the respective imaging blocks may be disposed in the capsule casing while making the upward and downward directions of the imaging devices differ by 180 degrees.

In the body-insertable apparatus according to the invention, each of the imaging devices of the respective imaging blocks may be arranged while making upward and downward directions of the imaging devices to be eccentric to the center of an axis of the body-insertable apparatus.

In the body-insertable apparatus according to the invention, each of the imaging devices of the respective imaging blocks may be horizontally-long devices each having a predetermined aspect ratio.

In the body-insertable apparatus according to the invention, imaging directions of each of the imaging devices of the respective imaging blocks may be set oblique direction to the center of an axis of the body-insertable apparatus.

In the body-insertable apparatus according to the invention, each of the imaging devices of the respective imaging blocks may be horizontally-long devices each having a predetermined aspect ratio, and disposed in the capsule casing while making upward and downward directions of the imaging devices differ by 90 degrees.

In the body-insertable apparatus according to the invention, each of the imaging devices of the respective imaging blocks may be generally square devices, and disposed in the capsule casing while making upward and downward directions of the imaging devices may differ by 45 degrees.

In the body-insertable apparatus according to the invention, the capsule casing may include a cylindrical body casing in which the respective imaging blocks may be disposed; and transparent end cover casings, provided watertight with the body casing, that may cover up the respective imaging blocks, and may derive illumination lights from the illuminating units, and wherein the body-insertable apparatus may further comprise an elastic member that urges each of the imaging blocks against each of the end cover casings opposed to the respective imaging devices.

In the body-insertable apparatus according to the invention, the elastic member may be a spring member.

The body-insertable apparatus according to the invention may further include a light-shielding member held among the imaging blocks.

In the body-insertable apparatus according to the invention, the light-shielding member may be a battery that supplies a power to the imaging devices and the illuminating units.

In the body-insertable apparatus according to the invention, the light-shielding member may be a substrate on which the imaging devices and the illuminating units are mounted.

In the body-insertable apparatus according to the invention, the capsule casing may include a cylindrical body casing in which the respective imaging blocks are disposed; and transparent end cover casings, provided watertight with the body casing, that covers up the respective imaging blocks, and derives illumination lights from the illuminating units, and wherein the body casing and one of the end cover casings may be formed integrally into a bottomed casing.

In the body-insertable apparatus according to the invention, the body casing of the bottomed casing may be made of a colored material impermeable to a visible light.

An in-vivo information acquiring system may include the body-insertable apparatus; an acquiring unit that acquires the images of the interior of the body cavity, the images being picked up at time series by respective imaging devices of the body-insertable apparatus; and a display controller that controls a display unit to display the images picked up and acquired by the respective imaging devices so as to correspond to a relationship among arrangement directions of the imaging devices.

In the in-vivo information acquiring system according to the invention, the display controller may control the images, picked up by the respective imaging devices made to coincide in upward and downward directions, to be displayed as they are.

In the in-vivo information acquiring system according to the invention, the display controller may control one of the images, picked up by the respective imaging devices made to coincide in upward and downward directions, to be displayed while being mirror-reversed.

In the in-vivo information acquiring system according to the invention, the display controller may control one of the images, picked up by the respective imaging devices made to relatively differ in upward and downward directions by 180 degrees, to be displayed while being reversed in upward and downward directions.

In the in-vivo information acquiring system according to the invention, the display controller may control one of the images, picked up by the respective imaging devices made to relatively differ in upward and downward directions by 90 degrees, to be displayed while being rotated by 90 degrees.

In the in-vivo information acquiring system according to the invention, the display controller may control one of the images, picked up by the respective imaging devices made to relatively differ in upward and downward directions by 45 degrees, to be displayed while being rotated by 45 degrees.

A method of manufacturing a compound-eye body-insertable apparatus for picking up the images of the interior of the body cavity at forward and backward in a movement direction of the capsule casing, the method includes disposing in a capsule casing a plurality of imaging blocks each including an illuminating unit that illuminates an interior of a body cavity and an imaging device that picks up images of the interior of the body cavity, the capsule casing including a cylindrical body casing, and transparent end cover casings, provided watertight with the body casing, that covers up the respective imaging blocks, and derives illumination lights from the illuminating units; forming a bottomed casing by bonding one of the end cover casings to the body casing; and loading one of the imaging blocks into the formed bottomed casing while positioning one of the imaging blocks to an axial direction and a circumferential direction to the center of an axis of the body-insertable apparatus, by dropping one of the imaging blocks into the bottomed casing from an opening of the body casing.

Effect of the Invention

According to the body-insertable apparatus, the in-vivo information acquiring system, and the method of manufacturing a body-insertable apparatus according to the present invention, the imaging devices of respective imaging blocks are disposed in the capsule casing while having a relationship between arrangement directions of the imaging devices. Therefore, a correspondence/positional relationship between the images picked up by the imaging devices is clear when a specific region such as an affected part in the body cavity is to be observed using the respective images forward and backward in the movement direction. It is, therefore, advantageously possible to facilitate close examination on the specific region using the both images, and easily make most use of the advantage of the compound-eye capsule endoscope capable of enlarging the field of view.

EXPLANATIONS OF LETTERS OR NUMERALS

Figure 1:
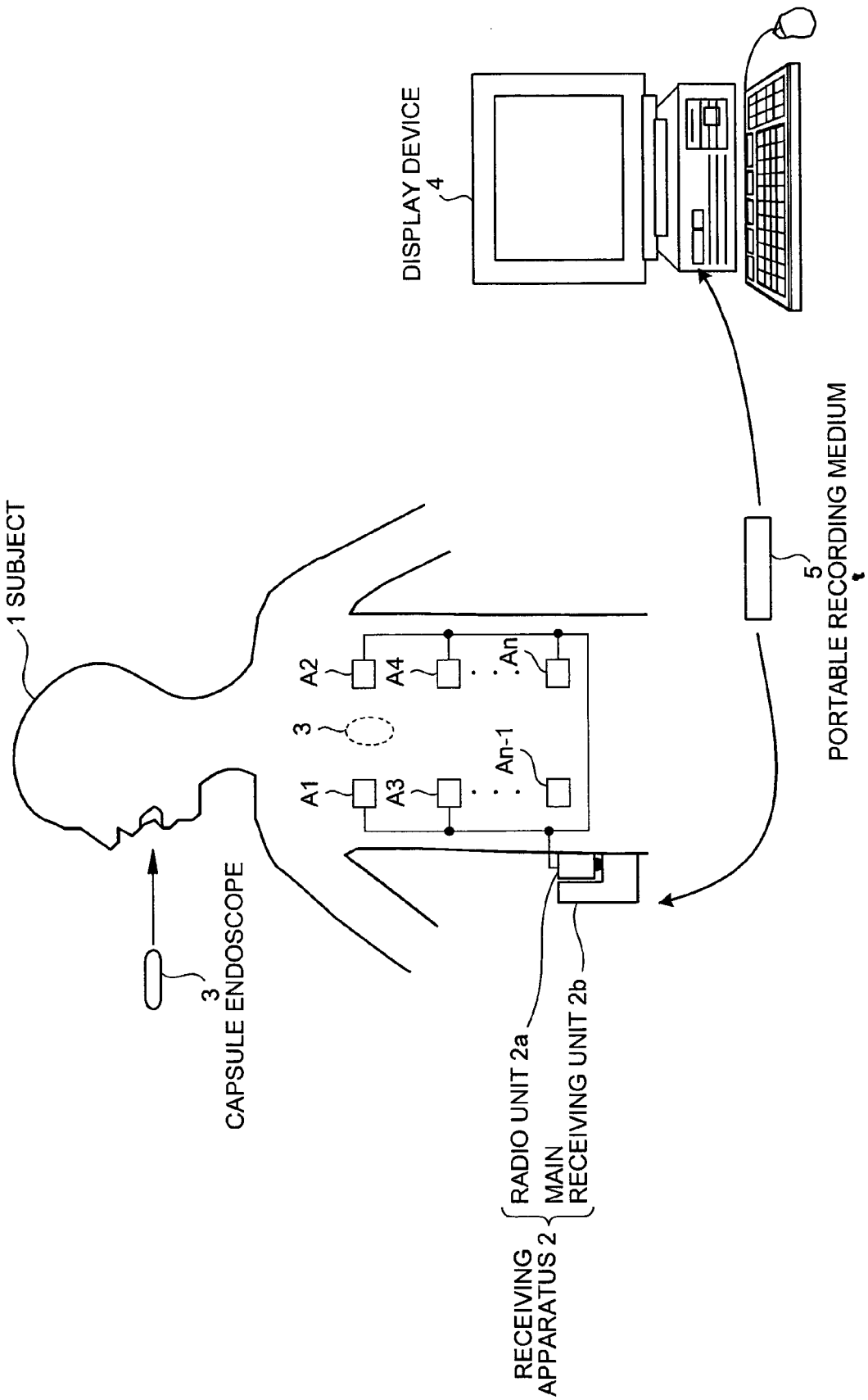
FIG. 1 is a pattern diagram showing an overall configuration of a radio in-vivo information acquiring system according to an embodiment of the present invention.

3 Capsule endoscope
11a, 11b Illuminating unit
12a, 12b Imaging device
14a, 14b Imaging block
16 Capsule casing
16a, 16b End cover casing
16c Body casing
16' Bottomed casing
29 Battery
30 Spring member
41 Input unit
42 Display unit
46 Display controller

BEST MODE(S) FOR CARRYING OUT THE INVENTION

A radio in-vivo information acquiring system as an exemplary embodiment of a body-insertable apparatus according to the present invention will be described hereinafter with reference to the accompanying drawings. It is to be noted that the present invention is not limited by the embodiment. In the drawings, same or corresponding constituent elements are denoted by the same reference symbols, respectively.

The embodiment of the present invention will be described. FIG. 1 is a pattern diagram showing an overall configuration of the radio in-vivo information acquiring system. The in-vivo information acquiring system uses a compound-eye capsule endoscope as an example of the body-insertable apparatus. As shown in FIG. 1, the radio in-vivo information acquiring system includes a capsule endoscope 3, which is inserted into the body of a subject 1, which picks up a body cavity image and radio-transmits data such as an image signal to the receiving apparatus 2, a receiving apparatus 2, which receives the data on the a body cavity image radio-transmitted from the capsule endoscope 3, a display device 4, which displays the body cavity image based on the image signal received by the receiving apparatus 2, and a portable recording medium 5, which mediates between the receiving apparatus 2 and the display device 4 for transmitting and receiving data between the receiving apparatus 2 and the display device 4. The receiving apparatus 2 includes a radio unit 2a including a plurality of receiving antennas A1 to An attached to the body surface of the subject 1, and a main receiving unit 2b that performs a processing and the like on a radio signal received through the receiving antennas A1 to An. These units are detachably connected to each other through a connector or the like. Alternatively, each of the receiving antennas A1 to An can be provided on, for example, a jacket which the subject can wear, and can be attached to the subject 1 by causing the subject 1 to wear the jacket. Moreover, in this alternative, the receiving antennas A1 to An can be detachably provided on the jacket.

The display device 4, which displays the body-cavity image picked up by the capsule endoscope 3, is configured, like a workstation or the like, to display images based on the data obtained by the portable recording medium 5. Specifically, the display device 4 can be configured to directly display images by a CRT display, a liquid crystal display or the like or to output images to the other medium.

A compact flash (registered trademark) memory or the like is used as the portable recording medium 5. The portable recording medium 5 is detachable from the main receiving unit 2b and the display device 4, and functions to be able to output or record information when being attached to the main receiving unit 2b or the display device 4. Specifically, the portable recording medium 5 is attached to the main receiving unit 2b while the capsule endoscope 3 is moving in body cavities of the subject 1, and the data transmitted from the capsule endoscope 3 is recorded in the portable recording medium 5. After the capsule endoscope 3 is discharged from the subject 1, that is, after the interior of the subject 1 is imaged, the portable recording medium 5 is detached from the main receiving unit 2b and attached to the display device 4. The display device 4 reads the recorded data. By allowing the portable recording medium 5 to mediate between the main receiving unit 2b and the display device 4 for transmitting and receiving data therebetween, the subject 1 can move freely while the body cavities are being imaged. The portable recording medium 5 also contributes to reduction in time for transmitting and receiving the data between the main receiving unit 2b and the display device 4. Alternatively, the other recording device included in the main receiving unit 2b can used to mediate between the main receiving unit 2b and the display device 4 for transmitting and receiving data therebetween, and the other recording medium can be connected to the display device 4 by wired or radio connection.

Figure 2:
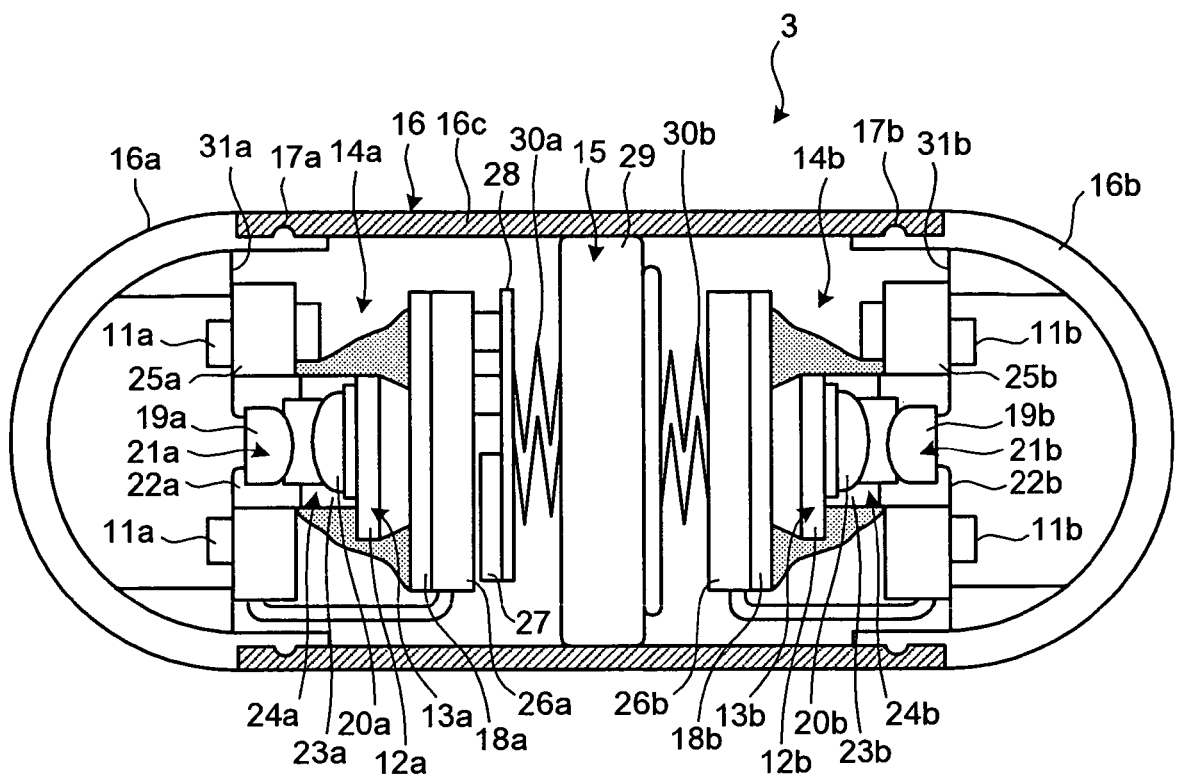
FIG. 2 is a cross-sectional view showing an internal configuration of a capsule endoscope.

Referring now to FIG. 2, the capsule endoscope 3 will be described. FIG. 2 is a cross-sectional view showing an internal configuration of the capsule endoscope 3. The capsule endoscope 3 is configured to include two imaging blocks 14*a* and 14*b*, which include illuminating units 11*a* and 11*b*, serving as illuminators, for illuminating the interior of each body cavity of the subject 1, and imaging devices 12*a* and 12*b*, e.g., CCDs or CMOSs, for picking up images of the body cavity, respectively, as well as a power supply unit 15 that supplies power to the imaging blocks 14*a* and 14*b* in a capsule casing 16.

The capsule casing 16 includes end cover casings 16*a* and 16*b*, which cover up the imaging blocks 14*a* and 14*b*, respectively and which are transparent and semicircular dome-shaped, and a cylindrical body casing 16*c*, which are provided to be watertight with the end cover casings 16*a* and 16*b* through concavo-convex engagement members 17*a* and 17*b* and in which the imaging blocks 14*a* and 14*b* are provided with a power supply unit 15 present therebetween, respectively. The capsule casing 16 is formed to be large enough to be swallowable from the mouth of the subject 1. The body casing 16*c* is made of a colored material that cannot transmit visible light.

The imaging units 13*a* and 13*b* include imaging devices 12*a* and 12*b* provided on imaging substrates 18*a* and 18*b* and imaging ranges illuminated by illumination lights from the illuminating units 11*a* and 11*b*, respectively, imaging lenses 21*a* and 21*b* forming subject images on the imaging devices 12*a* and 12*b* and including moving lenses 19*a* and 19*b* and fixed lenses 20*a* and 20*b*, respectively. The moving lenses 19*a* and 19*b* are fixed to moving frames 22*a* and 22*b*, the fixed lenses 20*a* and 20*b* are fixed to fixed frames 23*a* and 23*b*, thereby constituting focus adjusters 24*a* and 24*b*, respectively.

Furthermore, the illuminating units 11*a* and 11*b* are constituted by, for example, light-emitting diodes (LEDs), mounted on the illumination substrates 25*a* and 25*b*, and provided at four locations, i.e., upward, downward, left, and right locations around a center of an optical axis of the imaging lenses 21*a* and 21*b*, respectively. Moreover, in the imaging blocks 14*a* and 14*b*, signal processor/controllers 26*a* and 26*b* for processing or controlling the respective constituent elements of the blocks are provided on rear surfaces of the imaging substrates 18*a* and 18*b*, respectively. Furthermore, a radio substrate 28 on which a radio unit 27 including an antenna and the like for holding a radio communication with the outside is mounted, is provided in the signal processor/controller 26*a* of one imaging block 14*a*. The imaging substrates 18*a* and 18*b* are appropriately, electrically connected to the illumination substrates 25*a* and 25*b* by cables, respectively.

The power supply unit 15 located between the imaging blocks 14*a* and 14*b* is constituted by, for example, a button battery having a diameter almost identical to an inside diameter of the body casing 16*c*. As the battery 29, a silver oxide battery, a rechargeable battery, a power-generation battery or the like can be employed. In central portions between the imaging blocks 14*a* and 14*b* and the battery 29, spring members 30*a* and 30*b* each in the form of a torsion coil spring are provided to serve as elastic members that urge the respective imaging blocks 14*a* and 14*b* toward the end casings 16*a* and 16*b* opposed each other, that is, toward outside, respectively. The radio unit 27 on the radio substrate 28 is appropriately, electrically connected to the signal processor/controller 26*b* by a cable or the like passed through the outside of the battery 29. Likewise, the battery 29 is appropriately, electrically connected to the signal processors/controllers 26*a* and 26*b* and the like by cables or the like. The radio unit 27 can be provided for each of the imaging blocks 14*a* and 14*b* without being shared between the imaging blocks 14*a* and 14*b*.

Positioning units 31*a* and 31*b* are formed integrally near outer circumferences of interiors of the end cover casings 16*a* and 16*b*, respectively. By striking and thereby abutting a part of outer peripheral sides of the illumination substrates 25*a* and 25*b* against the positioning units 31*a* and 31*b*, respectively, the imaging blocks 14*a* and 14*b* are axially positioned in the capsule endoscope 3 based on the positioning units 31*a* and 31*b*. Furthermore, anti-rotation positioning units (not shown) are formed between the positioning units 31*a* and 31*b* and the illumination substrates 25*a* and 25*b*, respectively. The anti-rotation positioning units, each of which is constituted by a combination of convex and concave members engageable with each other, function to axially position the imaging blocks 14*a* and 14*b*, respectively.

Figure 3:
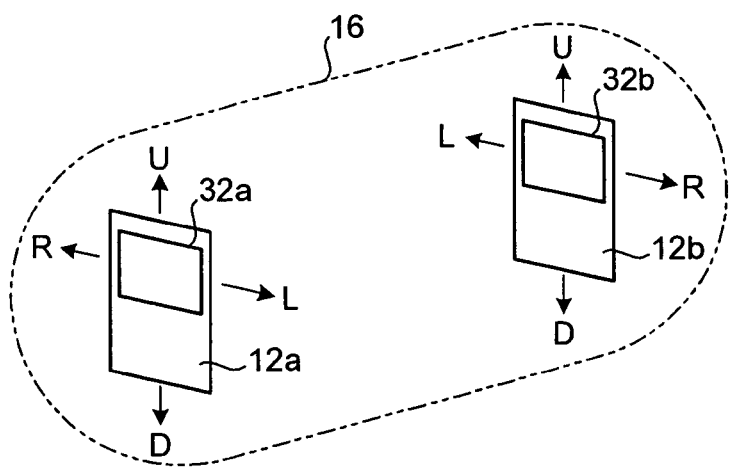
FIG. 3 is a schematic perspective view typically showing a first example of the arrangement relationship between imaging devices.

The arrangement relationship between the imaging devices 12*a* and 12*b* in the capsule endoscope 3 will next be described with reference to FIGS. 3 to 9. The imaging devices 12*a* and 12*b* are disposed in the capsule casing 16 associated therewith according to device characteristics such as imaging regions of the imaging devices 12*a* and 12*b*. FIG. 3 is a schematic perspective view typically showing a first example of the arrangement relationship between the imaging devices 12*a* and 12*b*. In the first example, devices which are identical in structure and two-dimensional imaging surfaces 32*a* and 32*b* of which are formed to be generally square are used as the imaging devices 12*a* and 12*b*, respectively. The imaging devices 12*a* and 12*b* are disposed in the capsule casing 16 to form the arrangement relationship therebetween so as to coincident in upward and downward directions with respect to center of axis direction. The imaging devices 12*a* and 12*b* are disposed in the capsule casing 16 while circumferential directions of the imaging devices 12*a* and 12*b* with respect to the center of axis direction being positioned so that, if upward, downward, left, and right directions of the forward-looking imaging device 12*a* are, for example, U, D, L, and R as shown in FIG. 3, respectively, upward and downward directions U and D of the backward-looking imaging device 12*b* coincide with those of the imaging direction 12*a* and so that only left and right directions L and R of the imaging device 12*b* are opposite to those of the imaging device 12*a*. It is to be noted that the upward, downward, left, and right directions of the imaging devices 12*a* and 12*b* are defined by the direction of a two-dimensional scan on the imaging surfaces 32*a* and 32*b* (that is, the direction of repeating a left-to-right scan thereon from upward to downward), and not by vertical direction.

Figure 4:
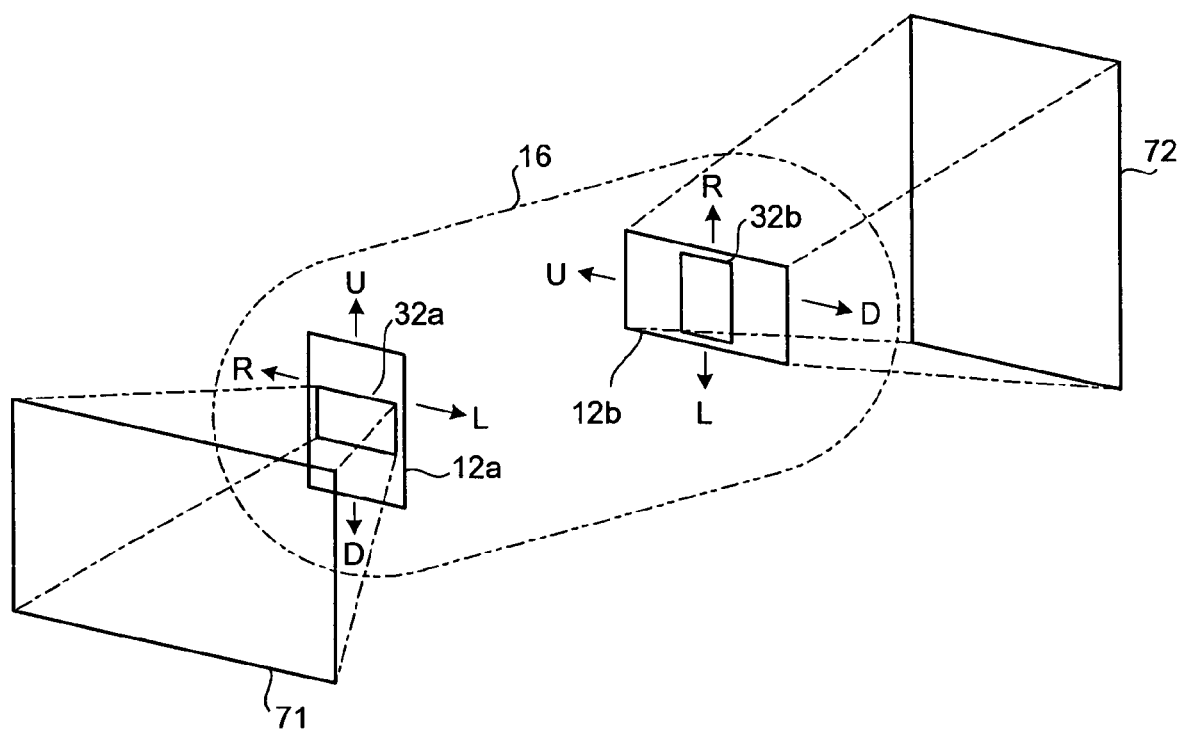
FIG. 4 is a schematic perspective view typically showing a second example of the arrangement relationship between imaging devices.

FIG. 4 is a schematic perspective view typically showing a second example of the arrangement relationship between the imaging devices 12*a* and 12*b*. In the second example, devices which are identical in structure and two-dimensional imaging surfaces 32*a* and 32*b* of each of which is formed horizontally long and has a predetermined aspect ratio are used as the imaging devices 12*a* and 12*b*, respectively. Examples of the predetermined aspect ratio include 4:3, 3:2, and 16:9. In the second example, the predetermined aspect ratio is, for example, 16:9.

In the second example, the imaging devices 12*a* and 12*b* are disposed in the capsule casing 16 to have the arrangement relationship so that the upward and downward directions of the imaging devices 12*a* and 12*b* are deviated by a predetermine dangle. Specifically, the imaging devices 12*a* and 12*b* are provided to differ in upward and downward directions by 90 degrees. The imaging devices 12*a* and 12*b* are disposed in the capsule casing 16 while circumferential directions of the imaging devices 12a and 12b with respect to the center of axis direction being positioned so that, if upward, downward, left, and right directions of the forward-looking imaging device 12a are, for example, U, D, L, and R as shown in FIG. 4, respectively, upward and downward directions U and D of the backward-looking imaging device 12b differ from those of the imaging device 12a by 90 degrees. Similarly to FIG. 3, the upward, downward, left, and right directions of the imaging devices 12a and 12b are defined by the direction of the two-dimensional scan on the imaging surfaces 32a and 32b (that is, the direction of repeating the left-to-right scan thereon from upward to downward) and not by the vertical direction.

Figure 6:
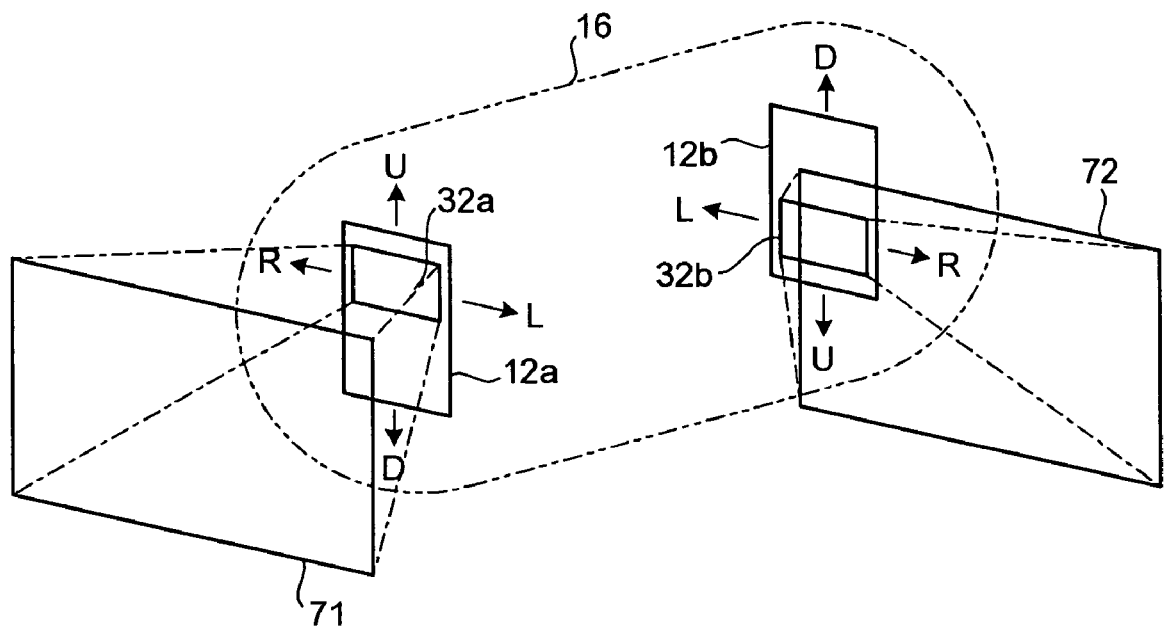
FIG. 6 is a schematic perspective view typically showing a third example of the arrangement relationship between imaging devices.

FIG. 6 is a schematic perspective view typically showing a third example of the arrangement relationship between the imaging devices 12a and 12b. In the third example, similarly to the second example, devices which are identical in structure and two-dimensional imaging surfaces 32a and 32b of each of which is formed horizontally long and has a predetermined aspect ratio, e.g., 16:9 are used as the imaging devices 12a and 12b, respectively.

In the third example, the imaging devices 12a and 12b are disposed in the capsule casing 16 to have the arrangement relationship therebetween so that the upward and downward directions of the imaging devices 12a and 12b are disposed eccentric to the center of an axis of the capsule endoscope 3, and deviated from each other by a predetermined angle. Specifically, the imaging devices 12a and 12b are provided while their upward and downward directions differ from each other by 180 degrees, i.e., while they are reversed with respect to each other. The imaging devices 12a and 12b are disposed in the capsule casing 16 while circumferential directions of the imaging devices 12a and 12b with respect to the center of an axis direction being positioned so that, if upward, downward, left, and right directions of the forward-looking imaging device 12a are, for example, U, D, L, and R as shown in FIG. 6, upward and downward directions U and D of the backward-looking imaging device 12b differ by 180 degrees from those of the imaging device 12a.

Figure 8:
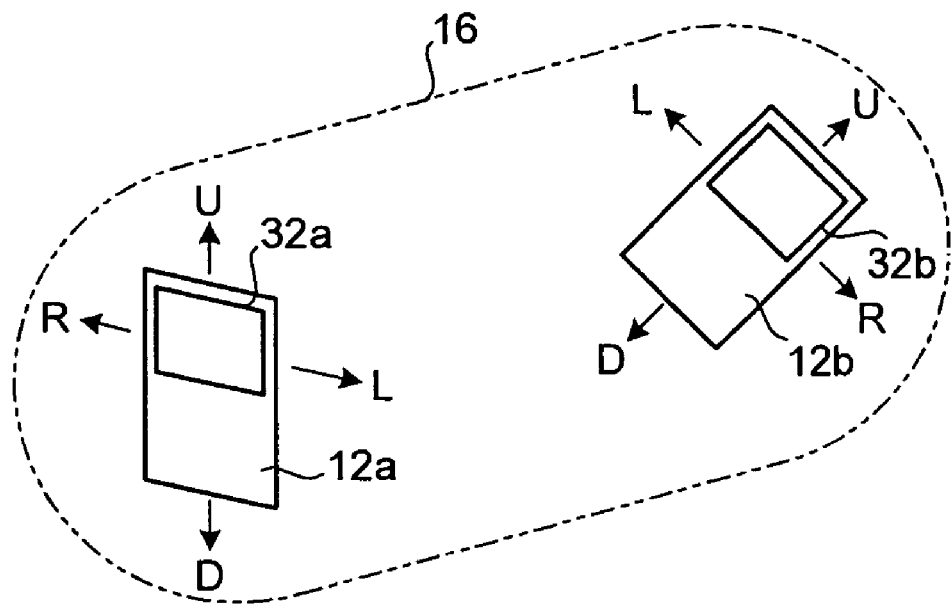
FIG. 8 is a schematic perspective view typically showing a fourth example of the arrangement relationship between imaging devices.

FIG. 8 is a schematic perspective view typically showing a fourth example of the arrangement relationship between the imaging devices 12a and 12b. In the fourth example, similarly to the first example, devices which are identical in structure and two-dimensional imaging surfaces 32a and 32b of which are formed to be generally square are used as the imaging devices 12a and 12b, respectively.

Such imaging devices 12a and 12b are disposed in the capsule casing 16 to have the arrangement relationship therebetween so as to deviate from each other in upward and downward directions by a predetermined angle. Specifically, the imaging devices 12a and 12b are provided to differ from each other in upward and downward directions by 45 degrees. The imaging devices 12a and 12b are disposed in the capsule casing 16 while circumferential directions of the imaging devices 12a and 12b with respect to the center of an axis direction being positioned so that, if upward, downward, left, and right directions of the forward-looking imaging device 12a are, for example, U, D, L, and R as shown in FIG. 8, upward and downward directions U and D of the backward-looking imaging device 12b differ from those of the imaging device 12a by 45 degrees.

The capsule endoscope 3 configured to be thus arranged sequentially moves in the body cavities after the subject 1 swallows the capsule endoscope 3 from his/her mouth at the time of carrying out an examination on the subject 1. During the movement of the capsule endoscope 3 in the body cavity such as the esophagus, a front image of the interior of the body cavity is picked up, for example, by the imaging device 12a while the illuminating units 11a of the imaging block 14a located forward illuminate a forward part in the body cavity, subjected to necessary processings by the signal processor/controller 26a, radio-transmitted to the receiving apparatus 2 by the radio unit 27, classified in a folder F1 as one frame image of the front image, and recorded in the portable recording medium 5 at certain timing. At another timing subsequent to the certain timing, a rear image of the interior of the body cavity is picked up by, for example, the imaging device 12b while the illuminating units 11b of the imaging block 14b located backward illuminate a backward part in the body cavity, subjected to necessary processings by the signal processor/controller 26b, radio-transmitted to the receiving apparatus 2 by the radio unit 27, classified in a folder F2 paired with the folder F1 as one frame image of the rear image, and recorded in the portable recording medium 5.

At this time, image-processing instruction information at the time of image display based on the arrangement relationship between the imaging device 12b and the imaging device 12a identified for every capsule endoscope 3 is also recorded, as header information for the folder F2, in a recording region of the portable recording medium 5 in which region the frame image transmitted from the imaging device 12b is recorded. For example, if the imaging devices 12a and 12b are arranged to relatively differ in upward and downward directions by 90 degrees as described in the second example, information on an instruction to perform a 90-degree rotation processing is additionally recorded as the header information. If the imaging devices 12a and 12b are arranged to relatively differ in upward and downward directions by 180 degrees as described in the third example, information on an instruction to perform a reversed processing between upward and downward directions is additionally recorded as the header information. If the imaging devices 12a and 12b are arranged to relatively differ in upward and downward directions by 45 degrees as described in the fourth example, information on an instruction to perform a 45-degree rotation processing is additionally recorded as the header information. If the imaging devices 12a and 12b are arranged to coincide in upward and downward directions as described in the first example, 'no processing' ('no instruction') can be set initially as information on an image processing instruction during image display. Furthermore, information on an instruction to perform a mirror-reversal processing can be additionally recorded as the header information according to a request from the user or the like.

In this manner, front images and rear images are alternately repeatedly picked up by the imaging devices 12a and 12b in a time-division fashion. By doing so, more images of even a region, e.g., the esophagus, through which the capsule endoscope 3 quickly passes within short time can be picked up by picking up images forward and backward in the direction of the movement of the capsule endoscope 3. Moreover, even if the region is asymmetric longitudinally, the field of view can be secured since the asymmetric region is observed from both forward and backward.

If the arrangement relationship between the two imaging devices 12a and 12b is not held so that the two imaging devices 12a and 12b are associated with each other, the following disadvantages occur. Even if abnormal sites such as lesion sites or bleeding sites are present in the images picked up by the respective imaging devices 12a and 12b, it is impossible to determine whether the sites are identical. This reduces the merit of the compound-eye capsule endoscope capable of imaging a region of interest in both forward and backward directions by half. If the imaging devices 12a and 12b picks up images of the bleeding site or a depressed (depressed lesion) site, in particular, it is difficult to determine how the images picked up by the respective imaging devices 12a and 12b are associated, as compared with a protruding portion such as a polyp. According to the first example of the capsule endoscope 3 in the embodiment, by contrast, the imaging devices 12a and 12b are disposed in the capsule casing 16 while having the arrangement relationship therebetween so as to coincide in upward and downward directions. Because of the clear correspondence and arrangement relationship between the imaging devices 12a and 12b, if a specific region such as an affected part in the body cavity is to be observed from the images forward and backward in the movement direction of the capsule endoscope 3, it is possible to easily, accurately determine whether the abnormal site present in the forward image is identical with that present in the backward image and to easily carry out a close examination on the specific region using the both images. In the first arrangement example, in particular, the imaging devices 12a and 12b are provided to be associated with each other so as to coincide in upward and downward directions. Therefore, the same region can be picked up twice only by changing imaging directions, so that the same region can be closely observed.

Figure 5:
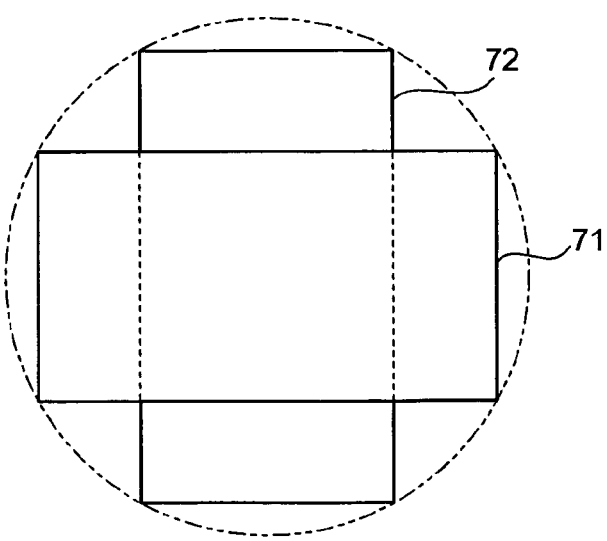
FIG. 5 is an explanatory view showing the positional relationship between imaging regions of the respective imaging devices in the second example.

In the second to fourth arrangement examples, the imaging ranges of the imaging devices 12a and 12b can be made associated with each other so as to mutually cover the field of view. It is, therefore, possible to secure a wide field of view in each of the body cavities. FIG. 5 is an explanatory view showing the positional relationship between imaging regions 71 and 72 of the imaging devices 12a and 12b in case of the second example. The horizontally long imaging regions 71 and 72 corresponding to the imaging devices 12a and 12b form an orthogonal arrangement relationship therebetween to correspond to the orthogonal arrangement relationship between the imaging devices 12a and 12b with respect to the axial direction of the capsule endoscope 3. The interior of the body cavity is imaged in this orthogonal arrangement relationship. An imaging region of the imaging lenses 21a and 21b is indicated by, for example, a broken-line circle in FIG. 5. In this case, each of the horizontally-long imaging devices 12a and 12b has insufficient coverage in upward and downward directions. However, by orthogonally arranging the imaging devices 12a and 12b and, therefore, making the imaging regions 71 and 72 orthogonal to each other, the imaging ranges (fields of view) of the imaging devices 12a and 12b can be made associated with each other so as to be able to mutually cover the regions which they cannot observe solely. It is, therefore, possible to image each body cavity while reducing the frequency of overlooking abnormal sites.

Figure 7:
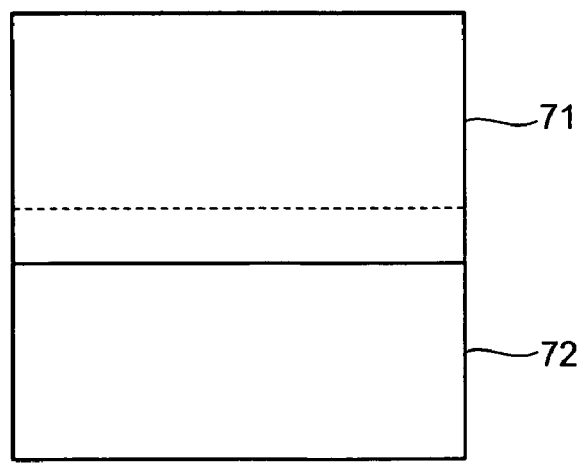
FIG. 7 is an explanatory view showing the positional relationship between imaging regions of the respective imaging devices in the third example.

Likewise, FIG. 7 is an explanatory view showing the positional relationship between imaging regions 71 and 72 of the imaging devices 12a and 12b in case of the third example. The horizontally-long imaging regions 71 and 72 corresponding to the imaging devices 12a and 12b form a upward and downward reversed arrangement relationship therebetween to correspond to the upward and downward reversed arrangement relationship between the imaging devices 12a and 12b with respect to the axial direction of the capsule endoscope 3. The interior of the body cavity is imaged in this upward and downward reversed arrangement relationship. An imaging region of the imaging lenses 21a and 21b is indicated by, for example, a broken-line circle in FIG. 7. In this case, each of the horizontally-long imaging devices 12a and 12b has insufficient coverage in upward and downward directions. However, by arranging the upward and downward directions of the imaging devices 12a and 12b to be eccentric to the center of axis of the capsule endoscope 3 and, therefore, setting the imaging regions 71 and 72 reversed directions between the upward and downward directions with respect to each other, the imaging device 12a images an upper side in the body cavity as the imaging region 71, and the imaging device 12b images a lower side as the imaging region 72. The imaging ranges (fields of view) of the imaging devices 12a and 12b can be made associated with each other so as to be able to mutually cover the regions which they cannot observe solely. It is, therefore, possible to image each body cavity while reducing the frequency of overlooking abnormal sites.

Figure 9:
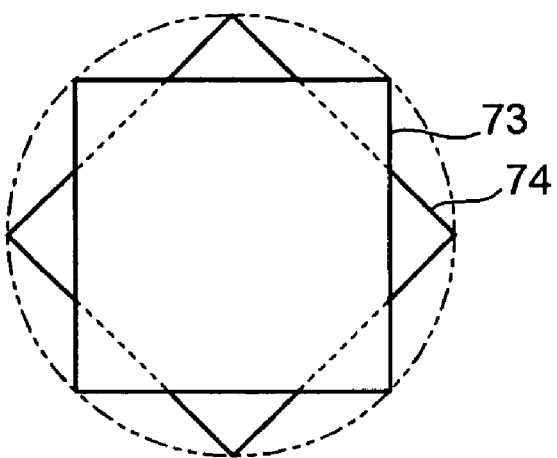
FIG. 9 is an explanatory view showing the positional relationship between imaging regions of the respective imaging devices in the fourth example.

Moreover, FIG. 9 is an explanatory view showing the positional relationship between imaging regions 73 and 74 of the imaging devices 12a and 12b. The imaging regions 73 and 74 corresponding to the imaging devices 12a and 12b form an arrangement relationship therebetween to correspond to the 45-degree-rotation arrangement relationship between the imaging devices 12a and 12b with respect to the center of axis direction of the capsule endoscope 3. The interior of the body cavity is imaged in this arrangement relationship. An imaging region of the imaging lenses 21a and 21b is indicated by, for example, a broken-line circle in FIG. 9. In this case, each of the imaging devices 12a and 12b has insufficient coverage in upward, downward, left, and right directions. However, by arranging the imaging devices 12a and 12b to be rotated by 45 degrees with respect to the imaging device 12b and vice versa, therefore, arranging the imaging regions 73 and 74 to be different by 45 degrees, the imaging regions of the imaging devices 12a and 12b are closer to the imaging region (circle) of the imaging lenses 21a and 21b. The imaging ranges (fields of view) of the imaging devices 12a and 12b can be made associated with each other so as to be able to mutually cover the regions which they cannot observe solely. It is, therefore, possible to image each body cavity while reducing the frequency of overlooking abnormal sites.

Furthermore, the body casing 16c is made of the colored material which is not transparent to the visible light. However, since the compound-eye capsule endoscope 3 includes a plurality of imaging blocks 14a and 14b, while one imaging device, e.g., the imaging device 12a is picking up an image, the illumination light from the illuminating unit 11b for the other imaging device 12b possibly enters the imaging region of the imaging device 12 as a stray light through a route of an internal clearance or the like. As a result, the quality of the picked-up image may possibly be degraded. The same thing is true for the relationship between the imaging device 12b and the illuminating unit 11a. According to the embodiment, by contrast, the battery 29 almost equal in diameter to the body casing 16c and present between the imaging blocks 14a and 14b functions as a light-shielding member. It is, therefore, possible to prevent degradation of the quality of the picked-up image because of the influence on one imaging device, of the illuminating light from the other imaging device when the imaging device 12a or 12b picks up an image. Alternatively, a substrate formed almost equal in diameter to the body casing 16c can be used as the light-shielding member either in place of or together with the battery 29.

Figure 10:
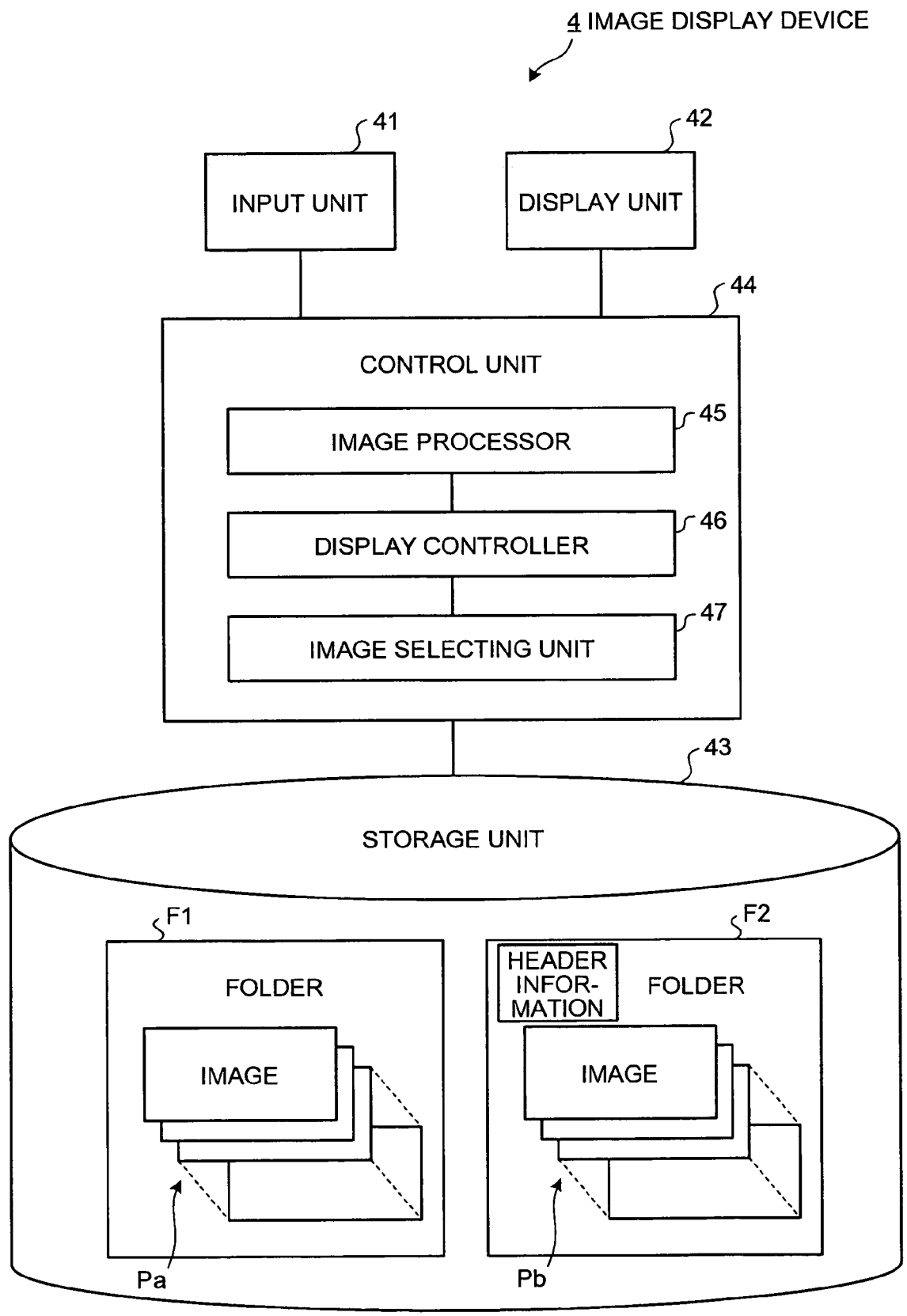
FIG. 10 is a block diagram showing a schematic configuration of a display device.

Referring to FIG. 10, the display device 4 will be described. FIG. 10 is a block diagram showing a schematic configuration of the display device 4 shown in FIG. 1. As shown in FIG. 10, the display device 4 includes an input unit 41, a display unit 42, a storage unit 43, and a control unit 44.

The input unit 41, which is realized by a pointing device such as a keyboard or a mouse, receives instruction information on an operation instruction to the display device 4 or on an instruction of processings performed by the display device 4, and transmits each instruction information to the control unit 44. The display unit 42, which is realized by a CRT display, a liquid crystal display or the like, displays instruction information from the input unit 41, an instruction result or the like. The display unit 42 includes predetermined image display regions in which image groups Pa and Pb stored in the paired folders F1 and F2 in the storage unit 43 are displayed in parallel, and the like.

The storage unit 43, which is realized by, for example, a hard disk device, holds various images acquired from the portable recording device 5. In the embodiment, for example, the image group Pa including a plurality of frame images picked up by the imaging device 12a in the capsule endoscope 3 is stored in the folder F1. The image group Pb including a plurality of frame images picked up by the imaging device 12b in the capsule endoscope 3 is stored in the folder F2 paired with the folder F1 for every capsule endoscope 3. Frame numbers are assigned to the respective images in the image groups Pa and Pb stored in the folders F1 and F2 in order of reception of image data by the receiving apparatus 2. Moreover, as already stated, the folder F2 includes a header-information storage region in which the image processing instruction information at the time of image display based on the arrangement relationship between the imaging devices 12a and 12b identified for every capsule endoscope 3 is stored.

The control unit 44 controls processings or operations performed by the input unit 41, the display unit 42, and the storage unit 43, respectively. The control unit 44 includes an image processor 45, a display processor 46, and an image selector 47. The image processor 45 functions to perform image processings such as a mirror-reversal processing, a upward and downward reversal processing, a 90-degree rotation processing, and a 45-degree rotation processing on each image. The image processor 45 appropriately performs the image processing on each frame image included in the image groups Pa and Pb. The display controller 46 functions to control a display processing performed by the display unit 42. In the embodiment, the display controller 46 particularly controls the display unit 42 to display images in parallel in a predetermined image display region based on the image groups Pa and Pb stored in the folders F1 and F2, respectively. The image selector 47 extracts and outputs the images one by one from the image groups Pa and Pb stored in the respective folders F1 and f2 according to frame rate in order of frame numbers so as to perform the image processing on or to display the images.

Figure 11:
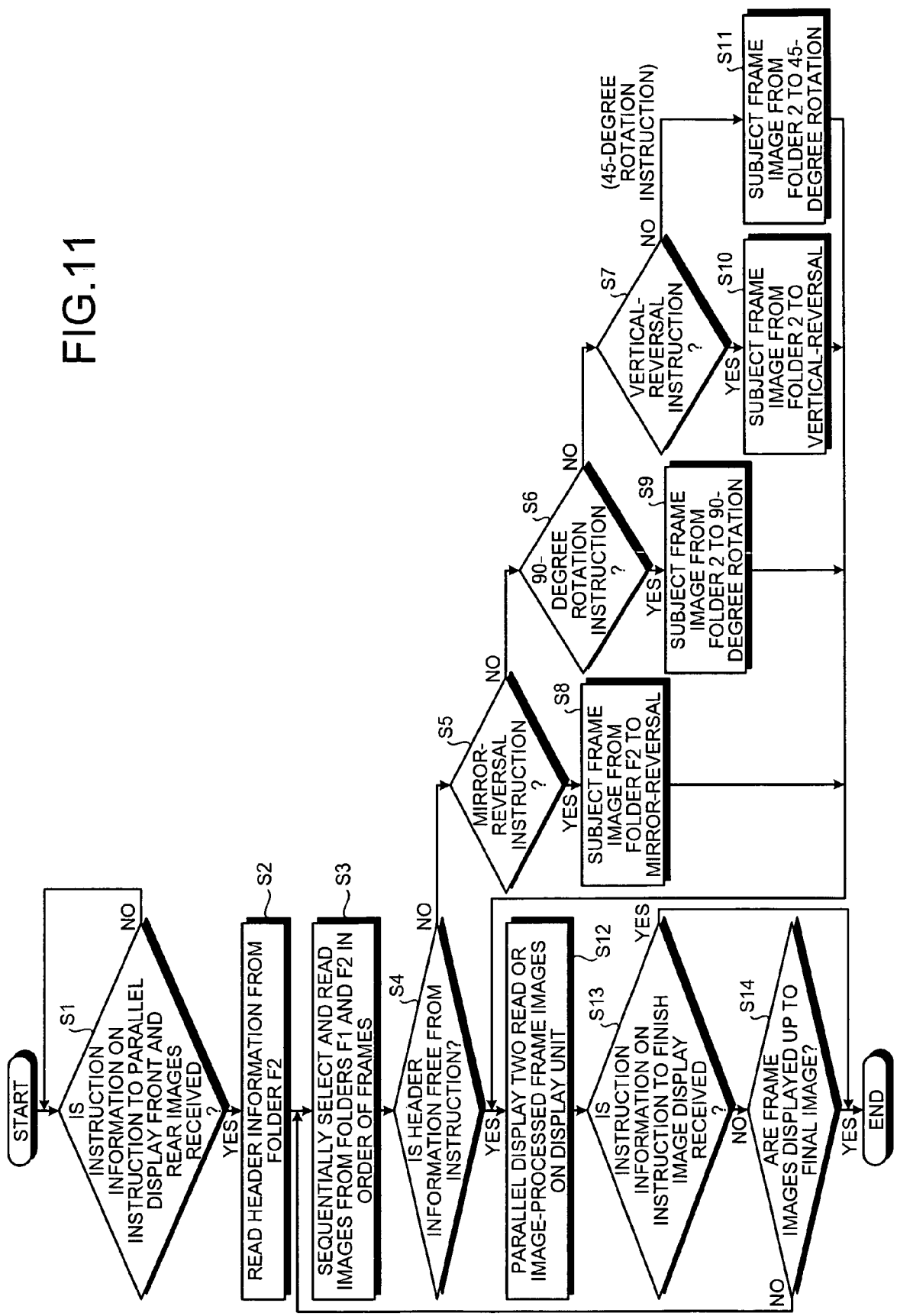
FIG. 11 is a schematic flowchart showing procedures of an image display processing performed by a display controller.

Referring next to FIG. 11, procedures of the image display processing performed by the display controller 46 will be described. Referring to FIG. 11, it is first determined whether instruction information on an instruction to display both a front image and a rear image picked up by the capsule endoscope in parallel is received from the input unit 41 (step S1). If it is determined that the instruction information is received (step S1: Yes), the display controller 46 instructs the image selector 47 to read header information from the header information storage region in the folder F2 (step S2), and to sequentially select and read the images in the image groups Pa and Pb stored in the respective folders F1 and F2 in order of frame number (step S3). The content of the header information in the header-information storage region in the folder F2 is determined (steps S4 to S7).

First, if this header information is free from instruction (step S4: Yes), the display controller 46 controls the display unit 42 to display the frame images read from the folders F1 and F2 in the image display region in parallel one by one without processing them (step S12). If the header information includes the mirror-reversal instruction (step S5: Yes), then the image processor 45 subjects the frame image read from the folder F2 to the mirror-reversal processing (step S8), and the display controller 46 controls the display unit 42 to display the frame image read from the folder F1 and the frame image read from the folder F2 and subjected to the mirror-reversal processing in the image display region in parallel (step S12).

If a 90-degree rotation instruction is stored (step S6: Yes), then the image processor 45 subjects the frame image read from the folder F2 to the 90-degree rotation processing (step S9), and the display controller 46 controls the display unit 42 to display the frame image read from the folder F1 and the frame image read from the folder F2 and subjected to the 90-degree rotation processing in the image display region in parallel (step S12).

If a upward and downward reversal instruction is stored (step S7: Yes), then the image processor 45 subjects the frame image read from the folder F2 to the upward and downward reversal processing (step S10), and the display controller 46 controls the display unit 42 to display the frame image read from the folder F1 and the frame image read from the folder F2 and subjected to the upward and downward reversal processing in the image display region in parallel (step S12).

If a 45-degree rotation instruction is stored (step S7: No), the image processor 45 subjects the frame image read from the folder F2 to the 45-degree rotation processing (step S11), and the display controller 46 controls the display unit 42 to display the frame image read from the folder F1 and the frame image read from the folder F2 and subjected to the 45-degree rotation processing in the image display region in parallel (step S12).

Thereafter, it is determined whether instruction information on an instruction to finish image display is received (step S13). If it is determined that this instruction information is received (step S13: Yes), the display controller 46 controls the display unit 42 to finish image display. If it is determined that the instruction information on the instruction to finish image display is not received (step S13: No), it is determined whether the display unit 42 displays the frame images up to the final frame image (step S14). If it is determined that the display unit 42 does not display the frame images up to the final frame image (step S14: No), the processing at and after the step S3 is repeatedly performed.

Figure 12:
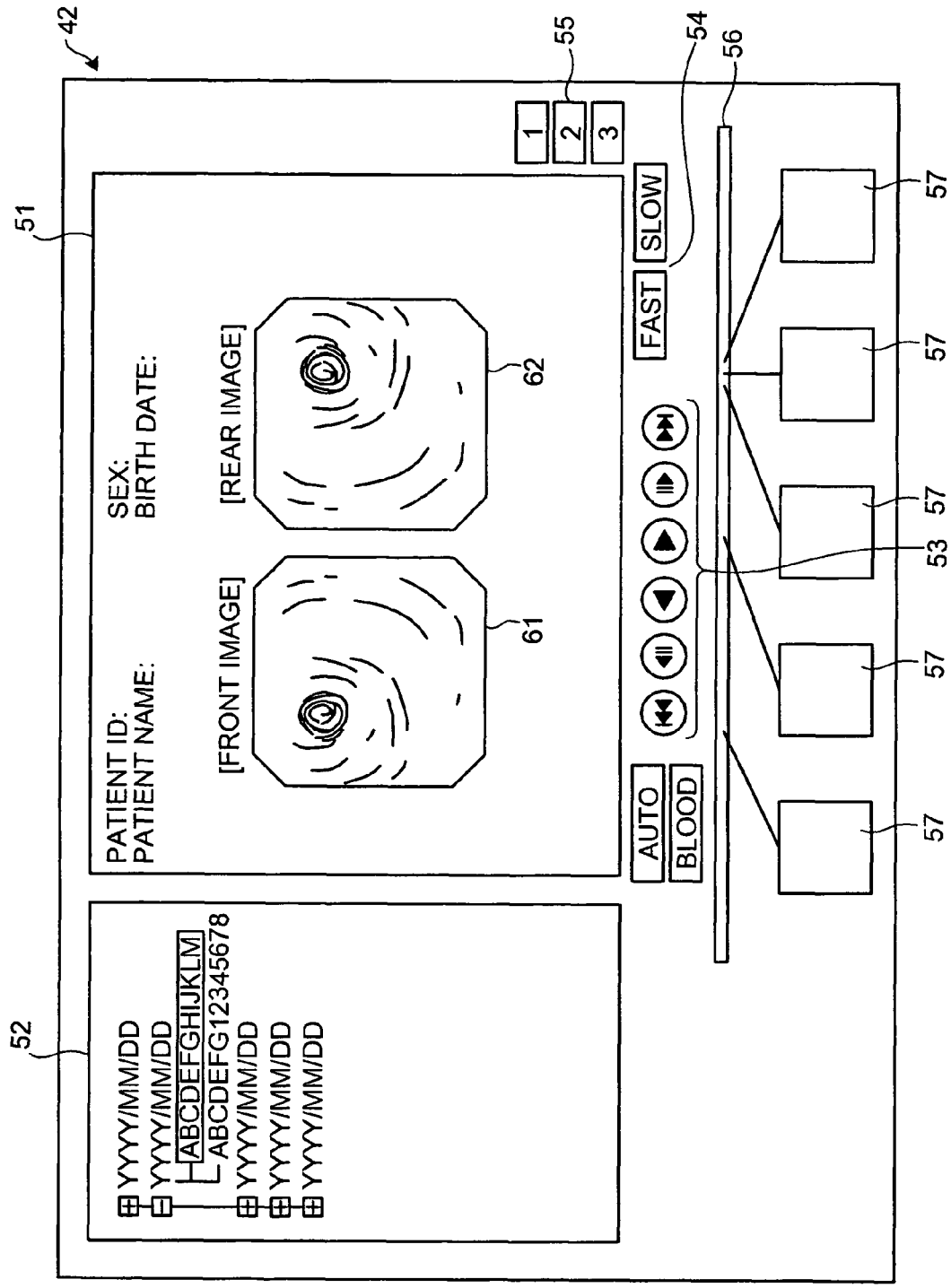
FIG. 12 is schematic view showing an example of a display screen of a display unit in case of the first arrangement example.

Referring next to FIGS. 12 to 15, examples of the images displayed in parallel on a display screen of the display unit 42 will be described. FIG. 12 is a schematic view showing an example of the display screen of the display unit 42 in case of the steps S4 and S12. The display screen of the display unit 42 includes a main observation monitor 51 for displaying examination images picked up by the imaging devices 12a and 12b. In the embodiment, using this main observation monitor 51, the images picked up by the imaging devices 12a and 12b are displayed in parallel.

In FIG. 12, reference symbol 52 denotes a filing list block for displaying a list of examination dates, and a list of patient names is displayed per examination date. If one patient name under one examination date is selected, a first image of the patient for an examination is displayed on the main observation monitor 51. Reference symbol 53 denotes a play controller for changing play methods on the main observation monitor 51, and the play controller 53 selectably includes PLAY, PAUSE, FRAME-BY-FRAME ADVANCE, PLAY TOP, PLAY END buttons and the like. If one play button is selected in the play controller 53, still images are continuously displayed on the main observation monitor 51, thereby pseudo-displaying a moving image. Reference symbol 54 denote a play-speed change button for changing over a play speed between two speeds of low speed/high speed. Reference symbol 55 denotes a number-of-displayed-images change button for changing the number of images to be displayed on the observation monitor 51 to one/two/four. For example, by selecting two as the number of displayed images and instructing two images to be displayed by this number-of-displayed-images change button 55, the examination images picked up by the imaging devices 121*a* and 12*b* are displayed left and right in parallel on the observation monitor 51. Reference symbol 56 denotes an image-processing mark bar an entire length of which is set to, for example, ten hours, and the image-processing mark bar 56 displays a temporal position of each image which is being played.

Reference symbol 57 denotes an image picked up by double-clicking on the image that is being displayed on the observation monitor 51. The image 57 is reduced-displayed in a selected image list block 58. At the same time, positions of the image-processing mark bar 56 corresponding to the selected images are connected to upper portions of the respective selected images by lines, thus clearly expressing a temporally positional relationship.

FIG. 12 shows an example in which a front image 61 and a rear image 62 picked up by the imaging devices 12*a* and 12*b* almost at the same timing are displayed side by side in parallel on the main observation monitor 51 according to the display control processing at the steps S4 and S12 shown in FIG. 11. Namely, the front image 61 is an example of the image obtained by causing the imaging device 12*a* to image a part in a forward direction in the body cavity, and the rear image 61 is an example of the image obtained by causing the imaging device 12*b* to image a part in a backward direction in the body cavity. In case of the first arrangement example, the images picked up by the imaging devices 12*a* and 12*b* are displayed without performing such a processing as rotation. Due to this, the forward image and the backward image are displayed in parallel as they are. However, it is determined that the arrangement relationship between the imaging devices 12*a* and 12*b* is such that they coincide in upward and downward directions and are opposite only in left and right directions. Therefore, the doctor or nurse who looks at the display screen shown in FIG. 12 can recognize that the correspondence/positional relationship between the two images 61 and 62 is bilateral symmetry. For example, the doctor or nurse can easily, accurately determine that an abnormal site appearing leftward in the front image 61 is identical with that appearing rightward in the rear image 62.

Figure 13:
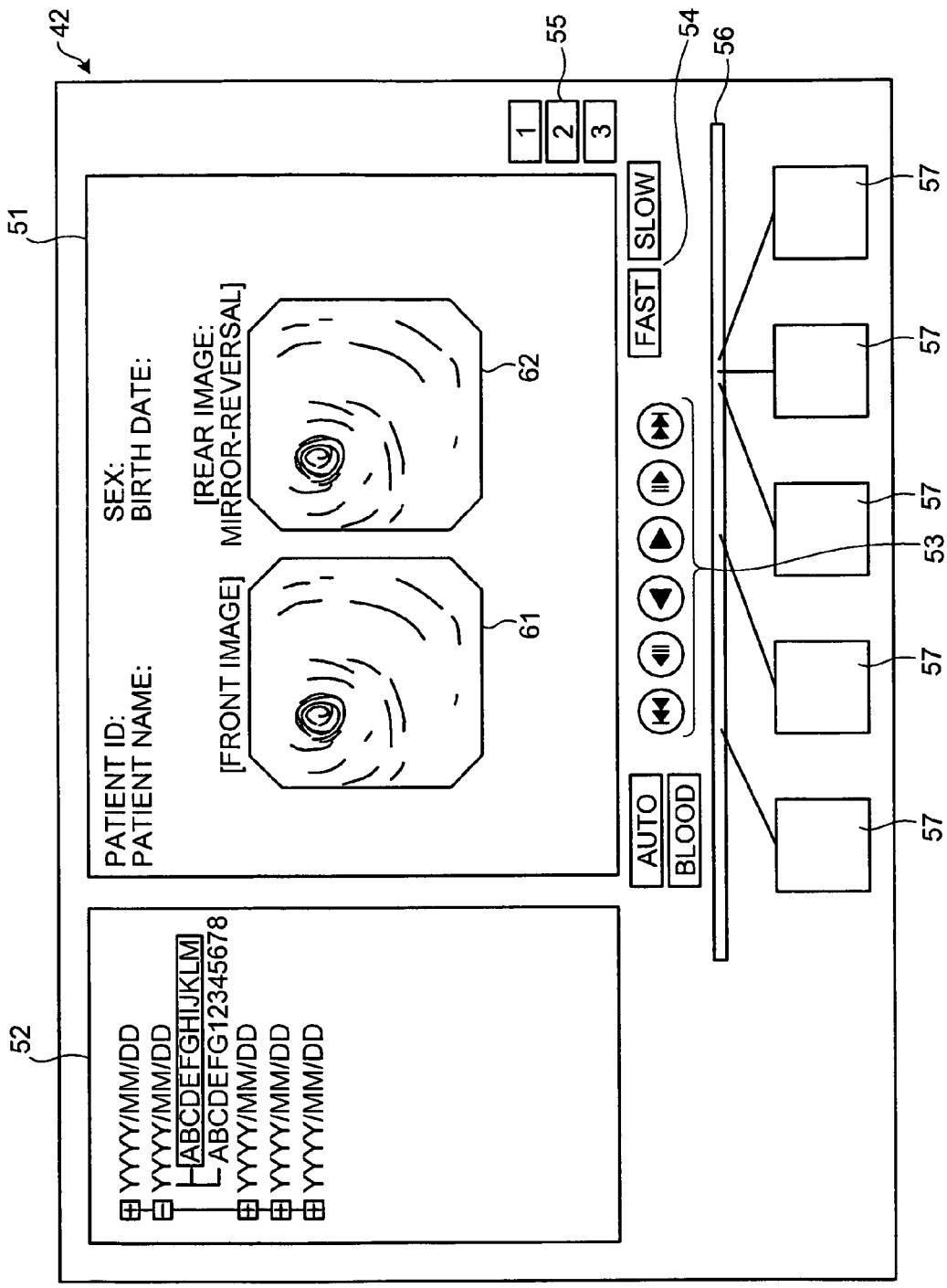
FIG. 13 is schematic view showing another example of the display screen of the display unit in case of the first arrangement example.

FIG. 13 is a schematic view showing an example of the display screen of the display unit 42 if information indicating the mirror-reversal processing is added as header information in response to a request from the user or the like in the first arrangement example (at the steps S5 and S12). In FIG. 13, images picked up by the imaging devices 12*a* and 12*b* are displayed in parallel using the main observation monitor 51. In comparison to FIG. 12, the rear image 62 obtained by causing the imaging device 12*b* to pick up a part in the body cavity in the backward direction is displayed in a mirror-reversed manner in FIG. 13. Namely, in the example of FIG. 12, the arrangement relationship between the imaging devices 12*a* and 12*b* is such that the imaging devices 12*a* and 12*b* coincide in upward and downward directions and are opposite only in left and right directions. On the other hand, in the example of FIG. 13, the image picked up by one imaging device 12*b* is mirror-reversed and the mirror-reversed image is displayed. Therefore, both the images 61 and 62 can be observed as if a car driver looks at rear side through a back mirror (looks at the rear image 62) while looking at front side through a front glass (looking at the front image 61), and the displayed images coincide in lateral direction. This can facilitate determining the correspondence/positional relationship between the images 61 and 62 and accelerate diagnosis. For example, it is possible to easily, accurately determine that an abnormal site appearing leftward in the front image 61 is identical with an abnormal site appearing leftward in the rear image 62.

Figure 14:
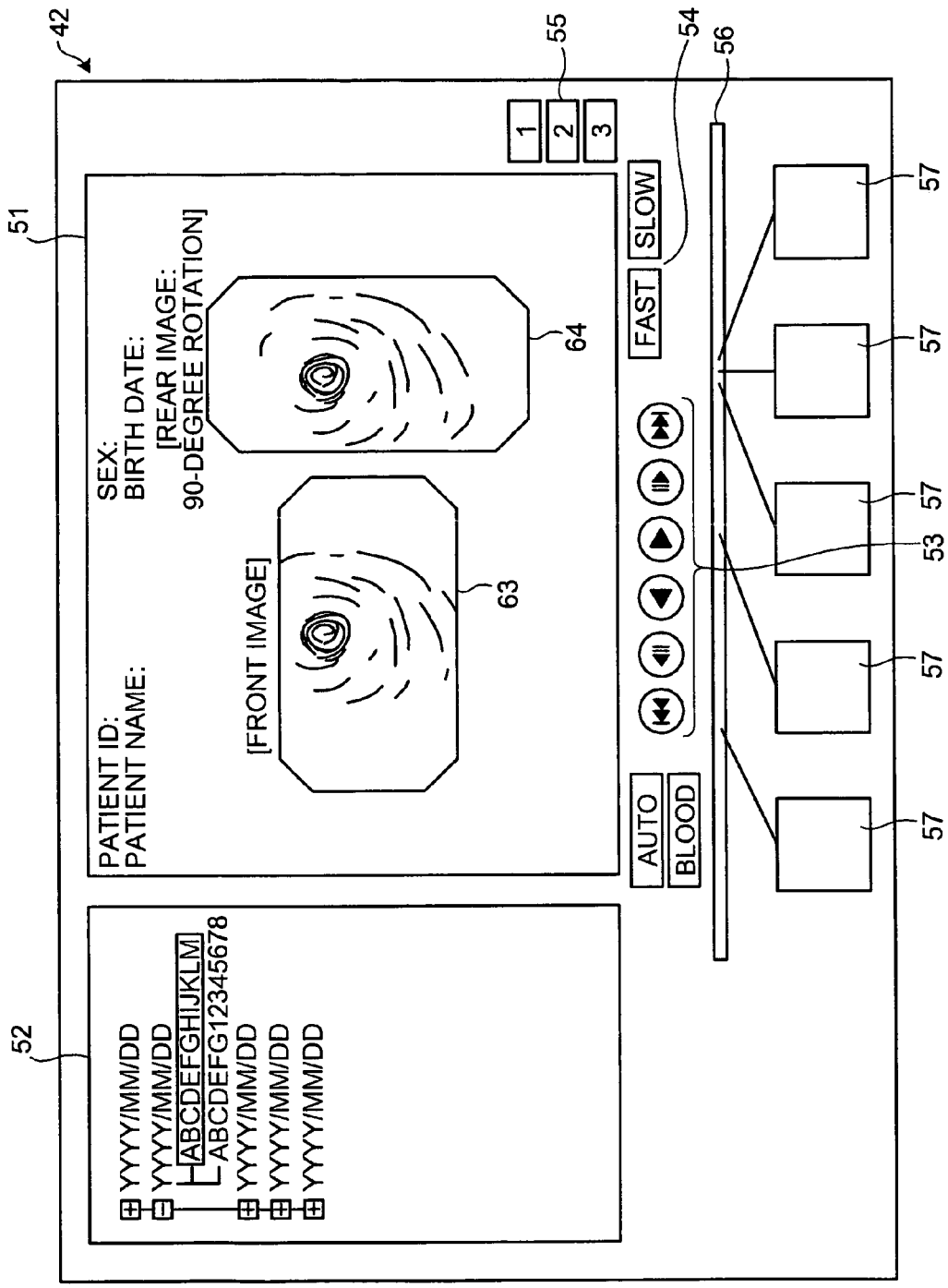
FIG. 14 is schematic view showing an example of the display screen of the display unit in case of the second arrangement example.

FIG. 14 is a schematic view showing an example of the display screen of the display unit 42 in case of the steps S6 and S12 accompanied by the 90-degree rotation instruction in the second arrangement example. In FIG. 14, images 63 and 64 picked up by the imaging devices 12*a* and 12*b* are displayed in parallel using the main observation monitor 51. In FIG. 14, the front image 63 picked up by one imaging device 12*a* is displayed as it is whereas the rear image 64 picked up by the other imaging device 12*b* is displayed as a vertically-long image by being rotated by 90 degrees. Namely, the imaging device 12*b* is provided while its upward and downward directions are rotated by 90 degrees. However, when the image picked up by the imaging device 12*b* is to be displayed, the upward and downward directions of the imaging device 12*b* is not corrected to coincide with display vertical direction but the image picked up by the imaging device 12*b* is displayed while its upward and downward directions are made to coincide with that in which the imaging device 12*a* picks up the image. By doing so, the images 63 and 64 are displayed in parallel while making the imaging devices 12*a* and 12*b* coincide in upward and downward directions in which the imaging devices 12*a* and 12*b* pick up the images 63 and 64, respectively. The correspondence/positional relationship between the images 63 and 64 is, therefore, easier to determine.

Figure 15:
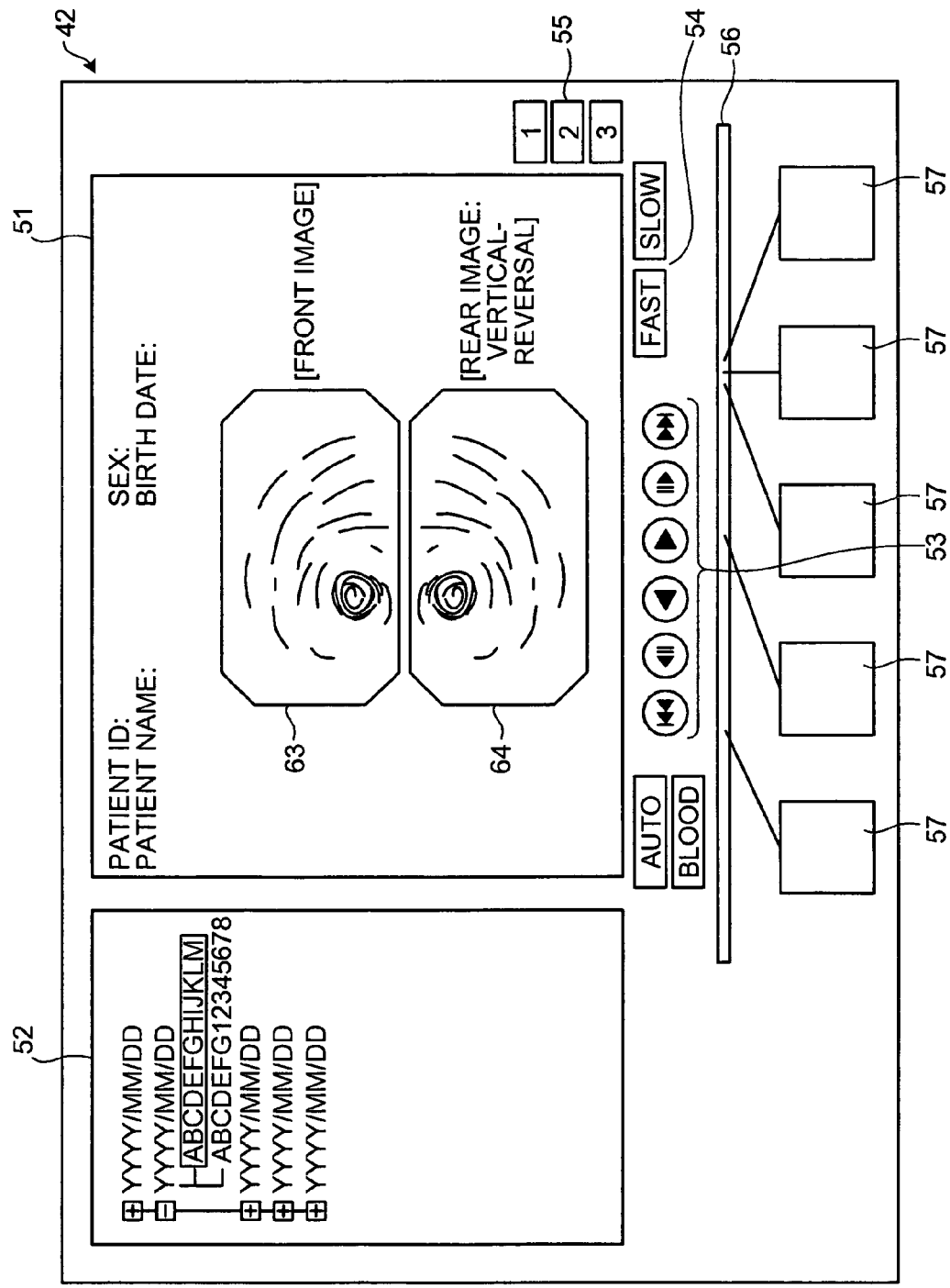
FIG. 15 is schematic view showing an example of the display screen of the display unit in case of the third arrangement example.

FIG. 15 is a schematic view showing an example of the display screen of the display unit 42 in case of steps S7 and S12 accompanied by the upward and downward reversal instruction in the third arrangement example. In FIG. 15, images 63 and 64 picked up by the imaging devices 12*a* and 12*b* are displayed above and below in parallel using the main observation monitor 51. In FIG. 15, the front image 63 picked up by the imaging device 12*a* is displayed as it is whereas the rear image 64 picked up by the other imaging device 12*b* is displayed while upward and downward directions being reversed to each other. Namely, the imaging device 12*b* is provided while its upward and downward directions are rotated by 180 degrees. However, when the image picked up by the imaging device 12*b* is to be displayed, the upward and downward directions of the imaging device 12*b* is not corrected to coincide with the display vertical direction but the image picked up by the imaging device 12*b* is displayed while its upward and downward directions are made to coincide with that in which the imaging device 12*a* picks up the image by the reversal processing of upward and downward directions. By doing so, the images 63 and 64 are displayed above and below in parallel while making the imaging devices 12*a* and 12*b* coincide in upward and downward directions in which the imaging devices 12*a* and 12*b* pick up the images 63 and 64, respectively. The correspondence/positional relationship between the images 63 and 64 is, therefore, easier to determine.

Figure 16:
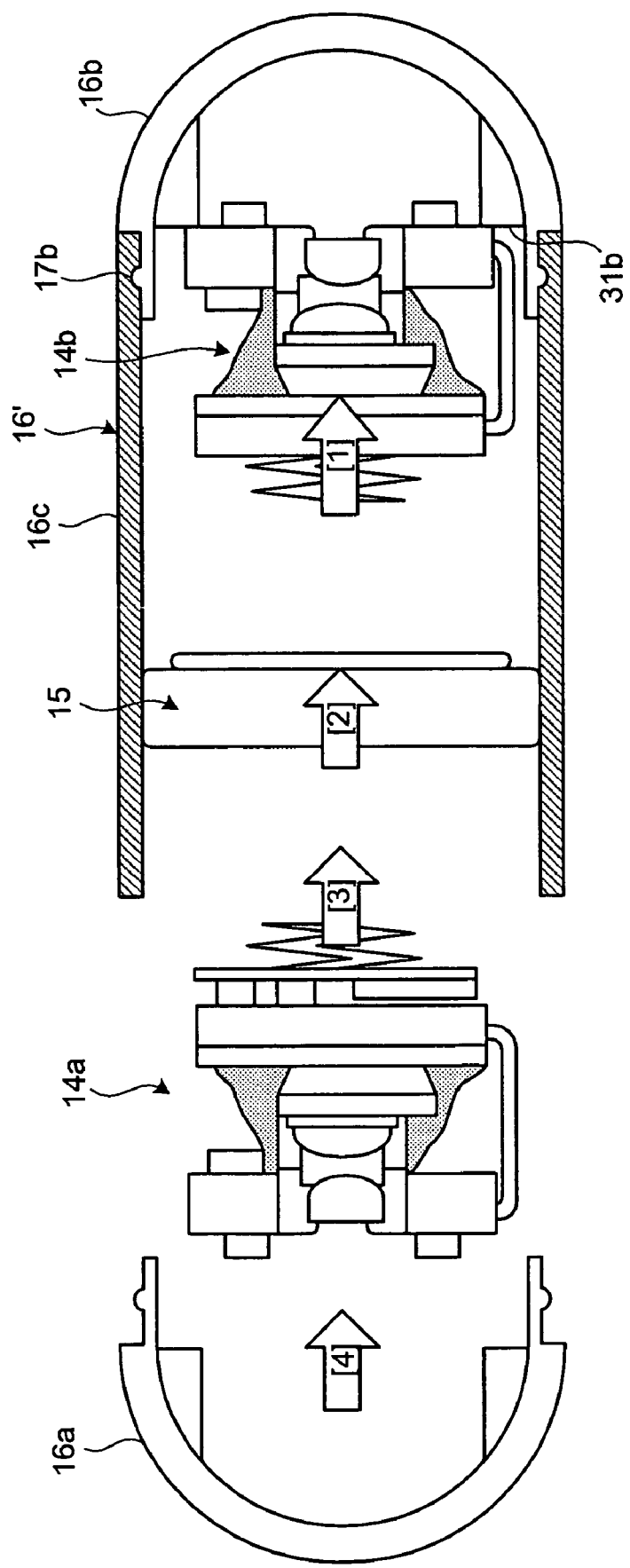
FIG. 16 is an exploded cross-sectional view showing a method of manufacturing a capsule endoscope.

Referring to FIG. 16, a method of manufacturing the capsule endoscope 3 according to the embodiment will be described. FIG. 16 is an exploded cross-sectional view showing the method of manufacturing the capsule endoscope 3 according to the embodiment. First, a bottomed casing 16' is formed by bonding one end cover casing 16*b* to the body casing 16*c* by adhesive (step [1]). The imaging block 14*b* is attached into the bottomed casing 16' by dropping the imaging block 14*b* from an opening 16*d* of the body casing 16*c*

(step [2]). By abutting and contacting the illumination substrate 25b of the imaging block 14b against and with the positioning unit 31b by the dropping operation, the imaging block 14b is axially positioned. At the same time, the anti-rotation positioning units are engaged with each other by slightly rotating the imaging block 14b in the bottomed casing 16', thereby positioning the imaging block 14b around the axis of the bottomed casing 16'. It is thereby possible to attach the imaging block 14b into the bottomed casing 16' with high assembly accuracy.

Subsequently to attachment of the imaging block 14b, the battery 29 is attached into the bottomed casing 16' by dropping the battery 29 thereinto (step [3]), the other imaging block 14a is attached into the bottomed casing 16's by dropping the imaging block 14a thereinto (step [4]), and the end cover casing 16a is bonded to the opening 16d of the body casing 16c (step [5]). The capsule endoscope 3 is thereby completed. Alternatively, the end cover casing 16a can be bonded to the opening 16d of the body casing 16c while the imaging block 14a is attached into the end cover casing 16a.

By abutting and contacting the illumination substrate 25a of the imaging block 14a against and with the positioning unit 31a by such an operation, the imaging block 14a is axially positioned. At the same time, the anti-rotation positioning units are engaged with each other by appropriately rotating the imaging block 14a in the bottomed casing 16', the imaging block 14a is positioned around the axis of the bottomed casing 16'. The imaging block 14a can be thereby attached into the bottomed casing 16' with high assembly accuracy.

If signs such as marks for positioning the anti-rotation positioning units are put between the body casing 16c and the respective end cover casings 16a and 16b, and positions of the anti-rotation positioning units of the end cover casings 16a and 16b are made to conform to each other in, for example, the first arrangement example, the imaging devices 12a and 12b of the imaging blocks 14a and 14b attached into the capsule casing 16 can be disposed to coincide in upward and downward directions with each other.

In case of the second arrangement example, the positions of the anti-rotation positioning units of the end cover casings 16a and 16b are made different from each other by 90 degrees, the imaging devices 12c and 12d of the imaging blocks 14a and 14b attached into the capsule casing 16 can be disposed to differ in upward and downward directions by 90 degrees. In case of the third arrangement example, the positions of the anti-rotation positioning units of the end cover casings 16a and 16b are made different from each other by 180 degrees, the imaging devices 12a and 12b of the imaging blocks 14a and 14b attached into the capsule casing 16 can be disposed to differ in upward and downward directions by 180 degrees. In case of the fourth arrangement example, the positions of the anti-rotation positioning units of the end cover casings 16a and 16b are made different from each other by 45 degrees, the imaging devices 12a and 12b of the imaging blocks 14a and 14b attached into the capsule casing 16 can be disposed to differ in upward and downward directions by 45 degrees.

In this manner, in the method of manufacturing the capsule endoscope 3 according to the embodiment, even if the capsule endoscope 3 is a compound-eye capsule endoscope, the bottomed casing 16' is formed in advance by bonding one end cover casing 16b to the body casing 16c. It is thereby possible to attach contents such as the imaging blocks 14b and 14a into the capsule casing 16 by dropping them from one direction, and to improve assembly performance. Furthermore, the imaging blocks 14a and 14b are positioned by the positioning unit 13a axially and around the axis of the capsule casing 16, and urged against the end cover casings 16a and 16b with the spring members 30a and 30b held between the battery 29 and the imaging blocks 14a and 14b, respectively. It is, therefore, possible to improve the assembly accuracy and maintain the high assembly accuracy.

First Modification

Figure 17:
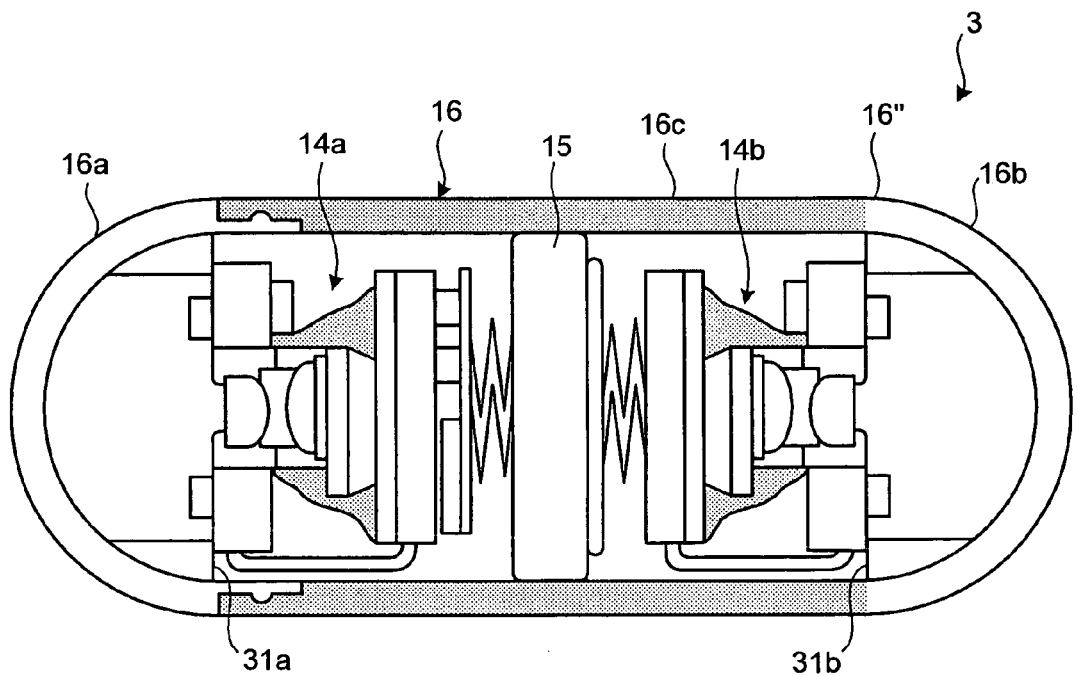
FIG. 17 is a cross-sectional view showing an example of a configuration of a capsule endoscope according to a first modification.

Referring to FIG. 17, a first modification will be described. FIG. 17 is a cross-sectional view showing an example of a configuration of the capsule endoscope 3 according to the first modification. In the embodiment, the bottomed casing 16' is formed by bonding one end cover casing 16b to the body casing 16c by adhesive. In the first modification, an end cover casing 16b' and a body casing 16c are integrally formed as a bottomed casing 16" in advance. By doing so, the capsule endoscope 3 can be assembled by dropping the imaging blocks 14a and 14b from one direction as described above with reference to FIG. 16.

In the bottomed casing 16", the end cover casing 16' is required to be transparent to the visible light, and the body casing 16c' is required not to be transparent to the visible light. Therefore, in the first modification, when the bottomed casing 16" is formed by integrating the end cover casing 16b' with the body casing 16c', the body casing 16c' is formed out of a colored material untransparent to the visible light by coinjection molding. Alternatively, the entire bottomed casing 16" can be formed integrally by a transparent material while either an interior or an exterior of the body casing 16c' is colored by applying paint thereto.

Second Modification

Figure 18:
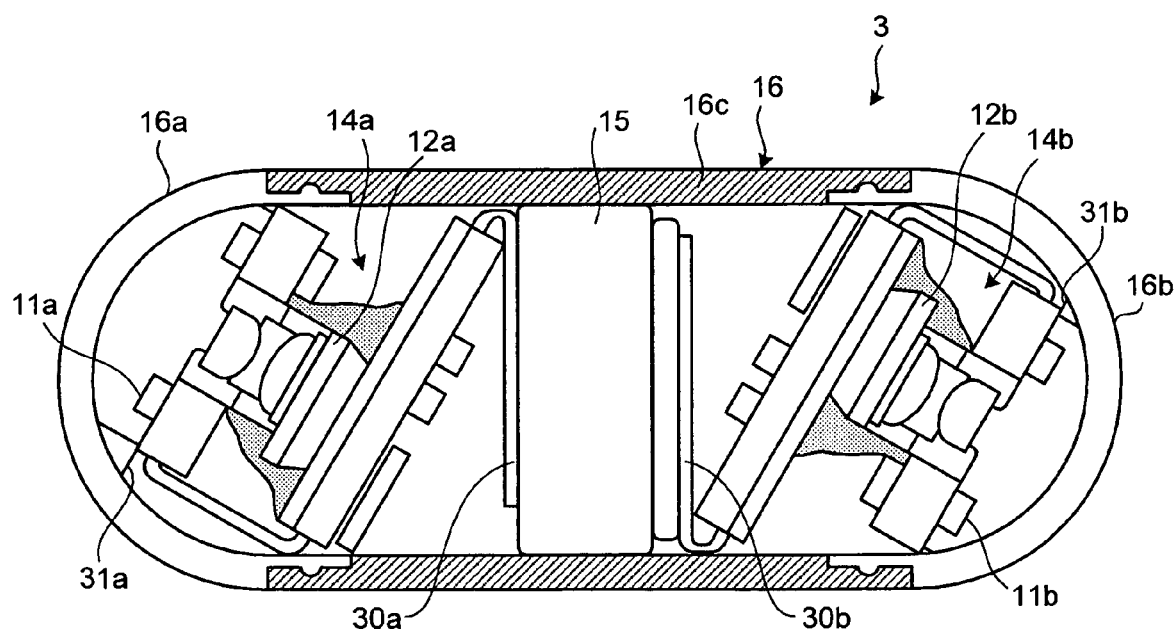
FIG. 18 is a cross-sectional view showing an example of a configuration of a capsule endoscope according to a second modification.

Referring to FIG. 18, a second modification will be described. FIG. 18 is a cross-sectional view showing an example of an internal configuration of the capsule endoscope 3 according to the second modification. The capsule endoscope 3 in the second modification is configured so that the imaging blocks 14a and 14b are disposed in the capsule casing 16 while optical axis directions (imaging directions) of the imaging blocks 14a and 14b are set not to parallel but oblique to the axis of the capsule casing 3. By arranging the imaging blocks 14a and 14b obliquely, the positioning units 31a and 31b of the end cover casings 16a and 16b are formed not to be orthogonal but to be oblique to the axis of the capsule endoscope 3. While the end cover casings 16a and 16b are bonded to the body casing 16c, the positioning units 31a and 31b are set to be parallel to each other. Furthermore, as the spring members 30a and 30b, doglegged springs are employed to urge the imaging blocks 14a and 14b against the oblique positioning units 31a and 31b, respectively.

Moreover, the imaging devices 12a and 12b included in the respective imaging blocks 14a and 14b are disposed in the capsule casing 16 while having the arrangement relationship therebetween so as to deviate in upward and downward directions by a predetermined angle. Specifically, the imaging devices 12a and 12b are provided to differ in upward and downward directions by 180 degrees, that is, vertically reversed with respect to each other. Similarly to the preceding embodiment, the images picked up by these imaging devices 12a and 12b can be displayed while, for example, the image picked up by the imaging device 12b is vertically reversed.

According to the second modification, the imaging directions of the respective imaging devices 12a and 12b are set obliquely to the axis of the capsule endoscope 3. Due to this, when the interior of the body cavity is to be imaged, an upper side in the body cavity can be imaged as a front image by the imaging device 12a and a lower side thereof can be imaged as a rear image by the imaging device 12b. It is thereby possible to reduce the frequency of overlooking abnormal sites in the body cavity.

The present invention is not limited to the above-stated embodiments and various modifications can be made of the present invention as long as they do not depart from the scope of the present invention.

INDUSTRIAL APPLICABILITY

As stated so far, the body-insertable apparatus, the in-vivo information acquiring system, and the method of manufacturing an in-vivo information acquiring system according to the present invention are suited as a compound-eye capsule body-insertable apparatus, a compound-eye in-vivo information acquiring system, and a method of manufacturing a compound-eye in-vivo information acquiring system capable of imaging a region of interest from both forward and backward and enlarging the field of view.

The invention claimed is:

1. A body-insertable apparatus comprising:
a plurality of imaging blocks;
a plurality of illuminating units;
a cylindrical body casing in which the imaging blocks and the illuminating units are disposed;
a plurality of transparent end cover casings, provided watertight with the body casing, that cover up the respective imaging blocks and the illuminating units; and
an elastic member that urges each of the imaging blocks against each of the end cover casings opposed to the respective imaging blocks.

2. The body-insertable apparatus according to claim 1, wherein the elastic member is a spring member.

3. The body-insertable apparatus according to claim 1, further comprising a light-shielding member held among the imaging blocks.

4. The body-insertable apparatus according to claim 3, wherein the light-shielding member is a battery that supplies a power to the imaging blocks and the illuminating units.

5. The body-insertable apparatus according to claim 3, wherein the light-shielding member is a substrate on which the imaging blocks and the illuminating units are mounted.

6. The body-insertable apparatus according to claim 1, wherein the body casing and one of the end cover casings are formed integrally into a bottomed casing.

7. The body-insertable apparatus according to claim 6, wherein the body casing of the bottomed casing is made of a colored material impermeable to a visible light.

8. The body-insertable apparatus according to claim 1, wherein the body casing provides a concave portion, the end cover casings provides a convex portion, and an elastic force of the elastic member is supported by a fitting between the concave portion and the convex portion.

9. The body-insertable apparatus according to claim 8, wherein the concave portion is provided on a fitting portion of the body casing almost circumferentially.

\* \* \* \* \*